(12) United States Patent
Williams (10) Patent No.: US 10,525,473 B2
(45) Date of Patent: Jan. 7, 2020

(54) SAMPLE COLLECTION KIT INCLUDING TWIST AND TEAR SOLUTION CAP

(71) Applicant: SPECTRUM SOLUTIONS L.L.C, Draper, UT (US)

(72) Inventor: Kevin Gregg Williams, Draper, UT (US)

(73) Assignee: SPECTRUM SOLUTIONS, L.L.C., Draper, UT (US)

( * ) Notice: Subject to any disclaimer, the term of this patent is extended or adjusted under 35 U.S.C. 154(b) by 156 days.

(21) Appl. No.: 15/667,228

(22) Filed: Aug. 2, 2017

(65) Prior Publication Data

US 2018/0036733 A1 Feb. 8, 2018

Related U.S. Application Data

(60) Provisional application No. 62/370,630, filed on Aug. 3, 2016, provisional application No. 62/510,174, filed on May 23, 2017.

(51) Int. Cl.
*B01L 3/00* (2006.01)
*G01N 1/38* (2006.01)

(52) U.S. Cl.
CPC .......... *B01L 3/523* (2013.01); *B01L 3/50825* (2013.01); *G01N 1/38* (2013.01);
(Continued)

(58) Field of Classification Search
CPC ............ B65D 51/2864; B65D 51/2871; B65D 51/2857; B65D 51/285; B65D 51/2842;
(Continued)

(56) References Cited

U.S. PATENT DOCUMENTS 3,712,296 A 1/1973 Gradone
3,792,699 A 2/1974 Tobin et al.
(Continued)

FOREIGN PATENT DOCUMENTS

CN 203101085 7/2013

OTHER PUBLICATIONS

Office Action issued in U.S. Appl. No. 14/952,712 dated Dec. 15, 2017.

*Primary Examiner* — Christopher Adam Hixson
(74) *Attorney, Agent, or Firm* — Workman Nydegger (57) ABSTRACT

A biological sample collection device can include a sample collection vessel having a sample collection chamber with an opening configured to receive a biological sample into the sample collection chamber. The sample collection chamber can also include elongate ridges disposed along and projecting inwardly from an interior portion thereof. The sample collection vessel can also include a connection member disposed on an exterior portion and a fluid reservoir. The fluid reservoir can include a reagent chamber having an open end and a closed end with an elongate member disposed at the closed end that is sized and shaped to engage the elongate ridges of the sample collection vessel when arranged within the fluid reservoir. The sample collection vessel can also include a sealing cap having internal threads for engaging external threads of the fluid reservoir and a complementary connection member to couple the sample collection vessel and the sealing cap.

19 Claims, 9 Drawing Sheets

(52) U.S. Cl.
CPC ... *B01L 2200/025* (2013.01); *B01L 2200/026* (2013.01); *B01L 2200/0689* (2013.01); *B01L 2200/16* (2013.01); *B01L 2300/042* (2013.01); *B01L 2300/0832* (2013.01); *B01L 2300/0858* (2013.01); *B01L 2400/0493* (2013.01); *G01N 2001/386* (2013.01)

(58) Field of Classification Search
CPC ............ B65D 51/2835; B65D 51/2828; B65D 51/2821; B65D 51/2807; B65D 55/08; B65D 55/12; B01L 3/523; B01L 3/50825; B01L 2400/0683; B01L 2300/042; B01L 2200/026; B01L 2200/025
See application file for complete search history.

(56) References Cited

U.S. PATENT DOCUMENTS

| | | |
|---|---|---|
| 3,800,781 A | 4/1974 | Zalucki |
| 3,966,558 A | 6/1976 | Calva-Pellicer |
| 4,311,792 A | 1/1982 | Avery |
| 4,877,037 A | 10/1989 | Ko et al. |
| 5,266,266 A | 11/1993 | Nason |
| 7,482,116 B2 | 1/2009 | Birnboim |
| 7,993,871 B2 | 8/2011 | Skiffington et al. |
| 8,696,595 B2 | 4/2014 | Sangha |
| 8,728,414 B2 | 5/2014 | Beach et al. |
| 9,523,115 B2 | 12/2016 | Birnboim |
| 9,732,376 B2 | 8/2017 | Oyler et al. |
| 2003/0143752 A1 | 7/2003 | Feldsine et al. |
| 2004/0014237 A1 | 1/2004 | Sugiyama |
| 2006/0216196 A1 | 9/2006 | Satoh |
| 2008/0058676 A1 | 3/2008 | Yong |
| 2008/0260581 A1 | 10/2008 | Rosman |
| 2009/0023219 A1 | 1/2009 | Perez |
| 2011/0021950 A1 | 1/2011 | Daniels |
| 2012/0220043 A1 | 8/2012 | Sangha |
| 2014/0051178 A1 | 2/2014 | Niggel et al. |
| 2014/0120531 A1* | 5/2014 | Biadillah ............ A61B 10/0051 435/6.1 |
| 2014/0194777 A1 | 7/2014 | Scampini et al. |
| 2015/0140681 A1* | 5/2015 | Meng .................... B01L 3/5023 436/501 |

\* cited by examiner

SAMPLE COLLECTION KIT INCLUDING TWIST AND TEAR SOLUTION CAP

CROSS-REFERENCE TO RELATED APPLICATIONS

This application claims the benefit of U.S. Provisional Patent Application Ser. No. 62/370,630 filed Aug. 3, 2016, and U.S. Provisional Patent Application Ser. No. 62/510,174 filed May 23, 2017, the disclosures of which are incorporated herein by reference in their entirety.

BACKGROUND

Technical Field

This disclosure generally relates to vials and vessels for collecting and storing biological samples. More specifically, the present disclosure relates to systems and kits for the collection and preservation of biological samples for future testing in a laboratory or other biological sample analysis facility.

Background and Relevant Art

Field collection of biological samples can provide scientists, physicians, geneticist, epidemiologists, or similar personnel with invaluable information. For example, access to a fresh sample of a patient's blood, purulent discharge, or sputum can help a physician or epidemiologist to isolate or identify a causative agent of infection. Similarly, a saliva sample can permit a scientist or geneticist access to the requisite nucleic acid for genetic sequencing, phylotyping, or other genetic-based studies. In the foregoing examples, in addition to many other situations, it is desirable to work with a fresh biological sample to ensure procurement of accurate results. However, isolation of the probative composition (e.g., nucleic acid, proteins, chemicals, etc.) often requires use of specialized equipment and often benefits from controlled laboratory conditions.

It can be inconvenient and sometimes improbable to require patients/individuals to travel to a biological sample collection center having the appropriate equipment and desirable controlled environment for sample preparation. Similarly, it may be difficult for personnel to directly access the patient/individual, particularly if the sample size is large and/or geographically diverse (e.g., as can be found in large genetic studies of thousands of individuals across an entire country, ethnic population, or geographic region). Further complicating this issue, it is often beneficial to immediately process any procured biological sample, and field personnel may be limited by lack of access to appropriate specialized equipment or to a controlled environment for high-fidelity sample processing.

Some biological sample collection devices and kits have addressed some of the foregoing issues. For example, some commercial kits provide a user with a vial for receiving a biological sample and a preservation reagent that can be added to the collected biological sample, acting to preserve elements within the biological sample (to a certain extent and for a period of time). However, implementation of self-collection systems often rely on inexperienced or untrained individuals to deposit the biological sample into the receiving vessel. This presents a number of problems, including, for example, technical training and precise measurements often required to properly preserve the biological sample for later processing. In the absence of such, it is important to provide a biological sample collection system that can be easily implemented by a novice user and which can preserve the received biological sample for later processing.

Accordingly, there are a number of disadvantages with biological sample collection and preservations systems that can be addressed.

BRIEF SUMMARY

Implementations of the present disclosure solve one or more of the foregoing or other problems in the art with kits, apparatuses, and methods for collecting and preserving a biological sample. In particular, one or more implementations can include a kit for collecting and preserving a biological sample. The kit can include a sample collection vessel having a sample collection chamber with an opening configured to receive a biological sample from a user. The sample collection vessel can also include one or more elongate ridges, other protrusion(s) and/or recess(es) disposed along and projecting or facing inwardly from an interior sidewall of the sample collection chamber and a connection member (e.g., one or more threads) disposed on an exterior portion of the sample collection vessel adjacent to the opening. The kit can also include a sealing cap having a sealing member, internal threads configured to engage the connection member of the sample collection vessel, and a reagent chamber. The reagent chamber itself can include a first end associated with the sealing member, a second end having an elongate or projecting member sized and shaped to engage the elongate ridge(s), other protrusion(s) and/or recesses of the sample collection chamber when arranged within the sample collection chamber, and an interior region or chamber comprising a measure of reagent(s).

The present disclosure also includes biological sample collection systems. In some embodiments, a biological sample collection system includes a sample collection chamber having an opening disposed at a top portion of the sample collection chamber and one or more elongate ridges, other protrusion(s) and/or recess(es) disposed along and projecting or facing inwardly from an interior sidewall, a reagent chamber selectively connected to the sample collection chamber that includes an elongate or projecting (e.g., T-shaped) member disposed at a closed end of the reagent chamber that is sized and shaped to engage the elongate ridge(s), other protrusion(s) and/or recess(es) of the sample collection chamber when arranged within the sample collection chamber, and a sealing cap having a connection mechanism configured to associate with and seal the sample collection chamber and/or the reagent chamber.

In some embodiments, the biological sample collection system includes a sample collection vessel, a fluid reservoir, and a sealing cap. The sample collection vessel can include a sample collection chamber having an opening that is configured to receive a biological sample into the sample collection chamber, one or more elongate ridge(s), other protrusion(s) and/or recess(es) disposed along and projecting or facing inwardly from an interior portion or sidewall of the sample collection chamber, and a connection member (e.g., one or more threads) disposed on an exterior portion of the sample collection vessel. The fluid reservoir can include a reagent chamber having an open end and a closed end. An elongate or projecting (e.g., T-shaped) member can be disposed at the closed end of the reagent chamber and sized and shaped to engage the elongate ridge(s), other protrusion(s) and/or recess(es) of the sample collection vessel when arranged within the sample collection chamber.

The fluid reservoir can also include external threads disposed on an exterior portion thereof. The sealing cap can include internal threads configured to engage the external threads of the fluid reservoir and a complementary connection member configured to associate with the connection member of the sample collection vessel to selectively couple the sample collection vessel and the sealing cap.

The present disclosure also includes methods for collecting and preserving a biological sample. An exemplary method includes receiving a biological sample from a user through an opening of a sample collection chamber, placing a fluid reservoir into the opening of the sample collection chamber, engaging an elongate or projecting member of the fluid reservoir with one or more elongate ridge(s), other protrusion(s) and/or recess(es) disposed along and projecting or facing inwardly from an interior portion or sidewall of the sample collection chamber, and rotating the fluid reservoir to release reagent(s) held within the fluid reservoir into the sample collection chamber. In some implementations, rotating the fluid reservoir causes the elongate or projecting member to become at least partially detached from the fluid reservoir, releasing the reagents through an aperture created by at least partial detachment of the elongate or projecting member. In other implementations, rotating the fluid reservoir causes a sidewall of the fluid reservoir to tear, releasing the contents held therein through the torn sidewall. In some embodiments, the sidewall can preferentially tear along a weakened or thinned portion of the sidewall.

Accordingly, systems, methods, and kits for collecting a biological sample are disclosed herein. This summary is provided to introduce a selection of concepts in a simplified form that are further described below in the detailed description. This summary is not intended to identify key features or essential features of the claimed subject matter, nor is it intended to be used as an indication of the scope of the claimed subject matter.

Additional features and advantages of the disclosure will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims, or may be learned by the practice of the disclosure as set forth hereinafter.

BRIEF DESCRIPTION OF THE DRAWINGS

In order to describe the manner in which the above recited and other advantages and features of the disclosure can be obtained, a more particular description of the disclosure briefly described above will be rendered by reference to specific embodiments thereof, which are illustrated in the appended drawings. It is appreciated that these drawings depict only typical embodiments of the disclosure and are not therefore to be considered to be limiting of its scope. The disclosure will be described and explained with additional specificity and detail through the use of the accompanying drawings in which.

DETAILED DESCRIPTION

Embodiments of the present disclosure address one or more problems in the art of systems, kits, and/or methods for collecting and preserving a biological sample. A biological sample can be collected and its contents evaluated for various reasons, including, for example, identifying or characterizing a causative agent of disease (e.g., for treatment of the affected individual, for epidemiological reasons, etc.) or for genetic analysis of a subject's nucleic acid (e.g., genetic phylotyping, gene expression studies, genome sequencing, etc.). In most instances, including within the foregoing examples, it is desirous that the fidelity of the biological sample is maintained so that it retains its probative value. However, collecting and preparing biological samples for analysis has traditionally been an endeavor for the skilled technician or specialized professional. This is problematic for obvious reasons, including the time and cost associated with individually collecting and transporting biological samples, particularly when the subjects reside in disparate rural locations and require service from personnel with the proper skill set to properly collect and preserve the biological sample.

Embodiments of the present disclosure provide sample collection and preservation systems and kits, and methods for using the same, which address one or more of the foregoing problems. For example, utilizing systems, kits, and methods for collecting and preserving biological samples, as disclosed herein, remove the need of specialized personnel when collecting and initially preserving a biological sample. Furthermore, sample collection and preservation is simplified, which decreases the likelihood that even an unskilled user will err when collecting and preserving a biological sample. As an illustrative example of the foregoing, biological sample collection kits disclosed herein include at least a two-piece sample collection and preservation system. A first portion includes a sample collection vial or vessel detachably associated with a funnel. The funnel acts to guide the receipt of a biological sample from a user into the sample collection chamber of the collection vial or vessel. The funnel makes it easier for a user to engage the collection vial and deposit a biological sample into the sample collection chamber. After depositing the requisite amount of biological sample, a user can remove the funnel and associate the second portion of the two-piece sample preservation system—e.g., a sealing cap associated with a reagent chamber—with the collection vial. The reagent chamber has been pre-filled with a predetermined amount of sample preservation reagent(s), and as the sealing cap is drawn down to seal the received biological sample within the sample collection chamber, the reagent(s) are released from the reagent chamber and into the sample collection chamber, mixing with and preserving the received biological sample.

As described in more detail below, the reagent chamber can be opened to release reagents into the sample collection chamber in a plurality of ways. In some embodiments, the reagent chamber is associated with a breakable tip, and when the sealing cap and reagent chamber are associated with the collection vial, the breakable tip is situated within the sample collection chamber where it can engage a protruding sidewall and/or recess to prevent further rotation of the sealing cap. The tip is breakable or removable so that with sufficient rotational force, it can be broken away or removed from the reagent chamber to allow further rotation of the sealing cap. With the tip shorn/broken off/removed, an opening or spout is revealed through which the reagent can be released into the sample collection chamber.

In some embodiments, the reagent chamber has a thinned or frangible sidewall such that when an elongate or projecting member associated with the reagent chamber engages ridges and/or recesses protruding or facing inwardly from the sidewall of the sample collection chamber, additional rotational force is transferred to—and ruptures—the thinned or frangible sidewall of the reagent chamber, thereby releasing the reagent(s) into the sample collection chamber. The reagent(s) mix with the biological sample and begin preserving one or more diagnostic components within the biological sample for later analysis.

As can be appreciated from the foregoing, in addition to alternative and/or additional embodiments provided herein, the systems, kits, and methods of the present disclosure can be used by skilled or unskilled individuals with reduced likelihood of error associated with collecting and at least initially preserving a biological sample. Accordingly, implementations of the present disclosure can reduce the cost associated with procuring biological samples for diagnostic, scientific, or other purposes and can increase the geographic reach of potential sample collection areas without the need of establishing the necessary infrastructure (e.g., controlled environments conducive to sample collection and preservation, skilled personnel to physically collect, transport, and/or preserve the biological samples, etc.).

As used herein, the term "biological sample" can include any cell, tissue, or secretory fluid (whether host or pathogen related) that can be used for diagnostic, prognostic, genetic, or other scientific analysis. This can include, for example, a human cell sample such as skin. It can also include a non-human cell sample that includes any of a bacterium, virus, protozoa, fungus, parasite, and/or other prokaryotic or eukaryotic symbiont, pathogen, or environmental organism. The term "biological sample" is also understood to include fluid samples such as blood, urine, saliva, and cerebrospinal fluid and extends to other biological samples including, for example, mucus from the nasopharyngeal region and the lower respiratory tract (i.e., sputum).

As used herein, the "probative component" of the biological sample refers generally to any protein, nucleic acid, surface moiety, or other compound that can be isolated from the biological sample. Preferably, the probative component is or includes nucleic acid, more preferably DNA. In a preferred embodiment, the biological sample is or includes saliva, which presumptively contains a preferable probative component in the form of the user's genetic material (e.g., DNA and RNA).

A Multi-Part Self-Contained Sample Collection Kit

In one embodiment, a biological sample is collected, preserved, and stored in a collection vial or vessel as part of a multi-piece, self-contained sample collection kit. A first piece includes a collection vial or vessel, a second piece includes a sample collection funnel, which may be packaged separately from or removably connected to the collection vial, and a third piece includes a solution reservoir disposed within or integrated with a sealing cap that is configured to associate with the collection vial, dispense sample preservation reagents into the collection vial, and seal the contents therein.

Figures 1A, 1B:
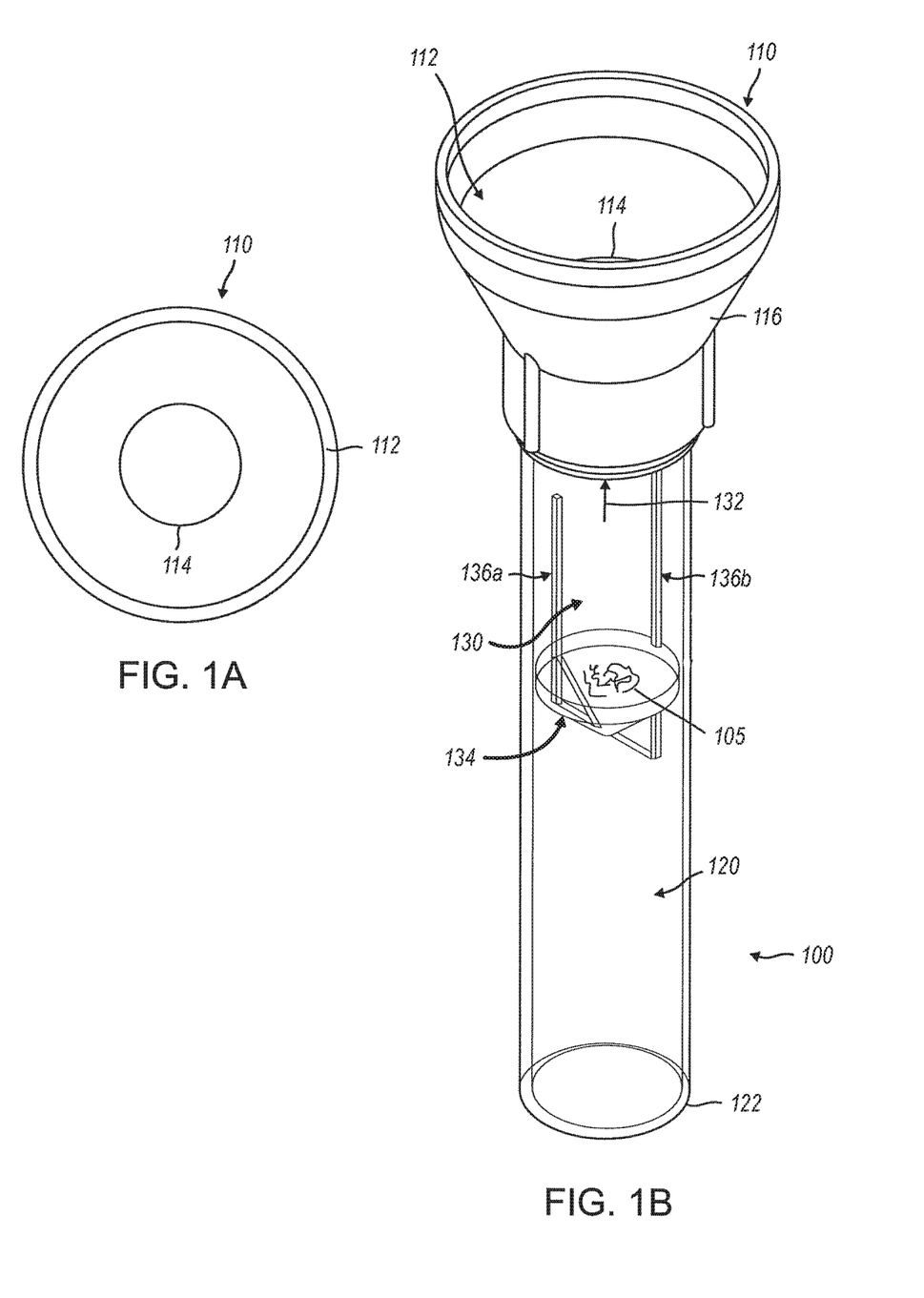
FIG. 1A illustrates a bottom view of a saliva funnel.
FIG. 1B illustrates a front perspective view of a saliva funnel removably attached to a sample collection vessel of the present disclosure.
Figure 2:
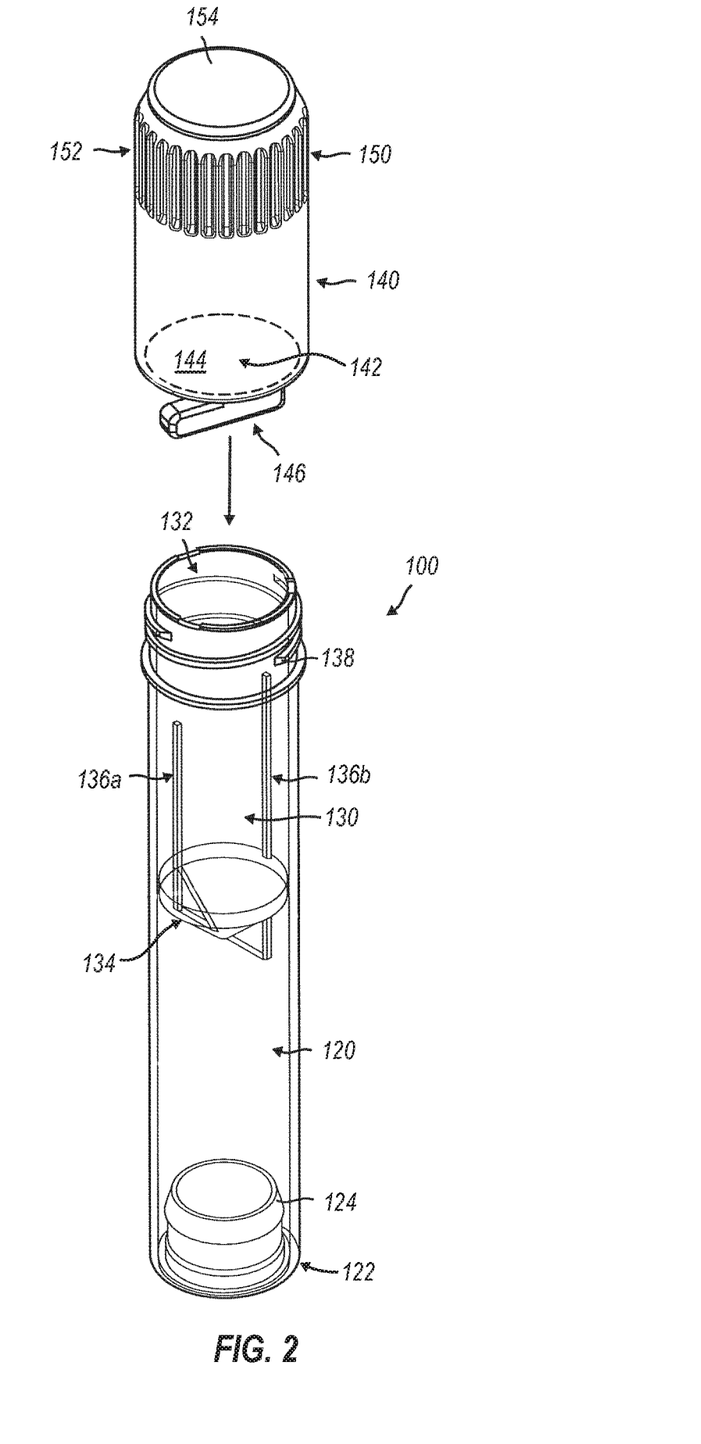
FIG. 2 illustrates an exploded front perspective view of an embodiment of a sample collection system.

For example, as shown in FIGS. 1A, 1B, and 2, a biological sample collection kit can include a collection vial 100 and a funnel 110, which can be associated with a top portion of the collection vial 100 and in fluid communication with a sample collection chamber 130 of the collection vial. The biological sample collection kit can also include a reagent chamber 140 having preservation reagent(s) 144 stored therein and which is associated with a solution cap 150. As shown in FIG. 2, for example, The solution cap 150—together with the reagent chamber 140—can be sized and shaped to associate with a top portion of the collection vial 100, fitting over and sealing an opening 132 in the sample collection chamber 130.

In some embodiments, the reagent(s) 144 within the reagent chamber 130 include a preservation or buffering solution that protect the integrity of the probative component of the biological sample prior to purification or testing. Preservation reagents are typically chemical solutions and may contain one or more salts (e.g., NaCl, KCl, $Na_2HPO_4$, $KH_2PO_4$, or similar, and which may, in some implementations, be combined as a phosphate buffered saline solution, as known in the art), lysing agents (e.g., detergents such as Triton X-100 or similar), chelating agents (e.g., ethylenediaminetetraacetic acid (EDTA), ethylene glycol-bis(β-aminoethyl ether)-N,N,N',N'-tetraacetic acid (EGTA), or similar), distilled water, or other reagents known in the art. In one or more embodiments, the reagent or buffering solution stabilizes at least one probative component within the sample (e.g., nucleic acids, such as DNA and RNA, protein, etc., and combinations thereof) during transfer, transportation, and/or storage at a laboratory, clinic, or other destination. In some embodiments, the sample can be stored, at or below room temperature after the preservation solution is added, for weeks or months without significant loss of the probative component. That is, the sample can still be utilized for diagnostic, genetic, epidemiologic, or other purposes for which it was collected after storage for weeks or months in the preservation solution.

With continued reference to FIGS. 1A, 1B, and 2, the solution cap 150 and saliva funnel 110 can each independently attach to the collection vial 100 using a connection mechanism. The connection mechanism can include, for example, threads, snap or press fit connections, tongue and groove members, bayonet connection, or other interlocking or mechanically coupling mechanisms. As shown in FIG. 1B, the funnel 110 is first attached to the collection vial 100 via complementary connection mechanisms (e.g., complementary threads). After facilitating receipt of a biological sample 105 from a user, the funnel 110 can be removed by reversing the complementary connection mechanism (e.g., unscrewing the funnel), and a solution cap 150 can be secured to the collection vial using a same or similar complementary connection mechanism, as shown in FIG. 2. That is, the solution cap 150 can include threads 156 located on an inner circumferential wall of the solution cap 150 that are complementary to and work in conjunction with the connection members 138 disposed on an exterior surface of the collection vial 100.

In some embodiments, the connection mechanism between the funnel and collection vial is different than the connection mechanism between the solution cap and the collection vial. For example, the funnel may be press fit or snap fit onto the collection vial, whereas the solution cap is rotationally secured through engagement of complementary threads located on an exterior portion of the collection vial and an interior portion of the solution cap. Regardless of the attachment mechanism used, a sample preservation fluid 144 can be introduced into the sample collection chamber 130 of the collection vial 100 and mixed with the deposited biological sample 105 as a result of the solution cap 150 being attached to the collection vial 100. As provided earlier, this can be due to the breaking off or removal of a breakable or removable tip 146 or due to a torn sidewall of the reagent vessel, or other means that causes stored reagent 144 to be released into the sample collection chamber 130.

As illustrated in FIG. 2, the solution cap 150 may additionally include a plurality of external ridges 152 that are located near solution cap top 154 of solution cap 150. The external ridges 152 can facilitate a user to better grip the solution cap 150 while positioning the cap 150 on top of collection vial 100. Additionally, or alternatively, the external ridges 152 can be used to rotate and close the solution cap 150 onto collection vial 100. In some embodiments, ridges 152 may be beneficial to enable the user to more forcefully torque the solution cap 150, and the external ridges 152 can provide the user with a better grip, enabling them to do so. Ridges 152 can also facilitate removal of the solution cap 150 at the laboratory when accessing the biological sample, such as manually or by an automated removal mechanism.

As can further be seen in FIGS. 1B and 2, the collection vial 100 can have a terminally closed end 122, which in some embodiments may be sealed with a removable plug 124. In some embodiments, the bottom portion 120 of the collection vial 100 and the sample collection chamber 130 are the same component such that the sealed bottom 122 of the collection vial 100 is the bottom of the sample collection chamber 130, and the sidewalls thereof define an uninterrupted space comprising the interior portion with an opening 132 disposed opposite the sealed bottom 122.

Thus, in some embodiments, the volume of the sample collection chamber 130 can be adapted to accommodate a smaller or larger volume of biological sample by altering the sizes of bottom portion 120 and/or chamber 130. A conical bottom 134 of the sample collection chamber 130 can, for example, be adjusted to various volumes. This can be done at the manufacturing stage or can be implemented as a selectively adjustable bottom to regulate the size (and volume) of the sample collection chamber 130. In some embodiments, the conical bottom 134 is stationary and immovable. Nonetheless, the volume of the sample collection chamber 130 can be varied at the manufacturing stage by increasing the dimensions of the collection vial 100.

Sample Collection Systems/Kits Having a Fluid Reservoir with a Breakable Tip

With continued reference to FIGS. 1A, 1B, and 2, and with additional reference to FIGS. 3-6, an exemplary method for implementing a multi-part sample collection kit as described above includes receiving a biological sample 105 through the funnel 110 connected to the collection vial 100. The received biological sample 105 can enter directly into the collection vial 100 or by gravitational flow along an interior funnel sidewall 116. The method can additionally include removing the funnel 110 from the collection vial 100 after facilitating receipt of the biological sample 105, and associating a solution cap 150 with the collection vial 100. The method can additionally include securing the solution cap 150 (e.g., by rotating the solution cap 150 along complementary threads between the cap 150 and the vial 100) to close the cap 150 over the top of the collection vial 100. The solution cap 150 can contain preservation reagent(s) 144 that are released as the solution cap 150 is rotated and closed over the collection vial 100. In some embodiments, a breakable or removable tip 146 located at the bottom, distal end of the reagent chamber 140 associated with the solution cap 150 is broken off or removed from the bottom of the reagent chamber 140 when the solution cap 150 is rotated and closed over the collection vial 150.

The aforementioned breakable tip 146 can have a laterally extending portion that is restrained or entrapped between two vertical ridges 136a, 136b positioned inside the sample collection chamber 130 of the collection vial 100. Ridges 136a, 136b act to initially restrain the breakable tip 146 from rotating when the solution cap 150 is rotated. However, after the solution cap 150 is rotated between a range of about 3 degrees to about 30 degrees (in some embodiments at least about 10 degrees) while the breakable tip 146 is rotationally restrained, the breakable tip 146 is broken off or removed, revealing an opening or spout 148 in the reagent chamber 140. This opening or spout 148 permits the reagent(s) 144 or preservation solution retained in the reagent chamber 140 of the solution cap 150 to be released into the sample collection chamber 130 and mix with the biological sample 105 received therein.

As provided farther below, in some embodiments, the tip is not broken off or removed entirely, but rather, rotational force applied to the rotationally restrained tip acts to tear a sidewall of a mechanically connected solution chamber, thereby releasing the reagents through the torn sidewall. The amount or extent of rotation following tip engagement with an elongate ridge can, in some embodiments, be proportional to the degree of tearing and can be influenced by the material used. For example, a greater extent of rotation can be associated with a larger tear in the sidewall, whereas a lesser extent of rotation can be associated with a respectively smaller tear in the sidewall. Further, if the material has a low tensile strength, it can tear more easily than if it had a high tensile strength or if it was highly elastic.

Although the figures illustrate sample collection chambers having elongate ridges disposed along and protruding from at least part of an interior sidewall of the sample collection chamber, it should be appreciated that the tip can be configured to engage other elements that may perform the same function. In some embodiments, one or more runnels or small grooves can be formed within the interior sidewall of the sample collection chamber that are configured in size and shape to receive the tip or elongate member of the reagent chamber. Upon association of the tip or elongate member with the groove, it can be rotationally restrained, similar to the tip engagement of the elongate ridges, as provided above.

Figure 3:
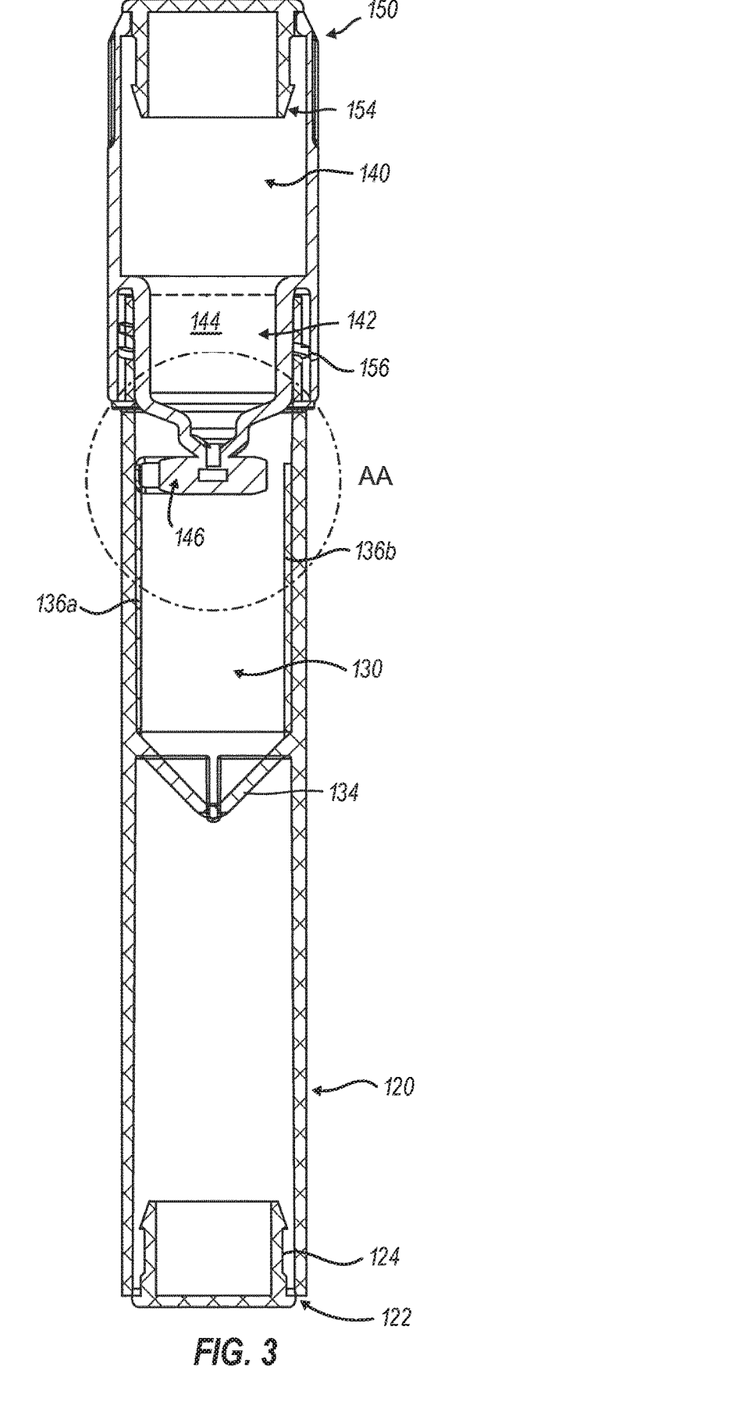
FIG. 3 illustrates a partially assembled, cross-sectional view of the sample collection system of FIG. 2.
Figure 4:
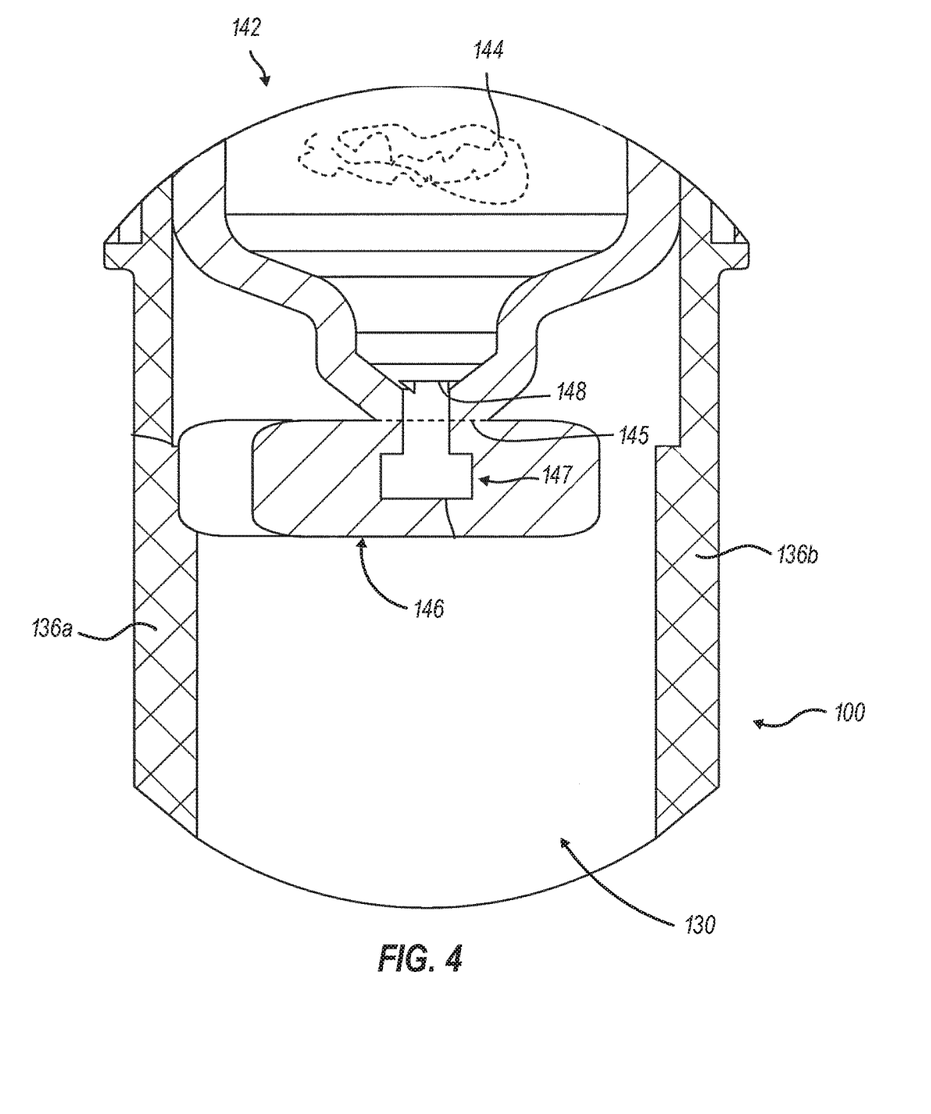
FIG. 4 illustrates a close-up view of area AA of FIG. 3, showing an elongate or projecting member with one side of the elongate or projecting member associating with an elongate ridge within the sample collection chamber.

As illustrated in FIGS. 3 and 4, the collection vial 100 can include a breakable tip 146 that is configured to engage an elongate ridge 136a or 136b extending inwardly away from the sidewall of the sample collection chamber 130 and into the sample. As perhaps better illustrated by FIG. 4, which represents a zoomed-in area AA of FIG. 3, the breakable tip 146 can include a single elongate body that extends to interact with either one of the ridges 136a, 136b of the sidewall. Once the breakable tip 146 has engaged the elongate ridge 136a, 136b, additional rotational force in the direction of the engaged breakable tip 146 will cause the breakable tip 146 to break or shear off from the associated reagent chamber 140 (e.g., along dashed line 145).

Figure 5:
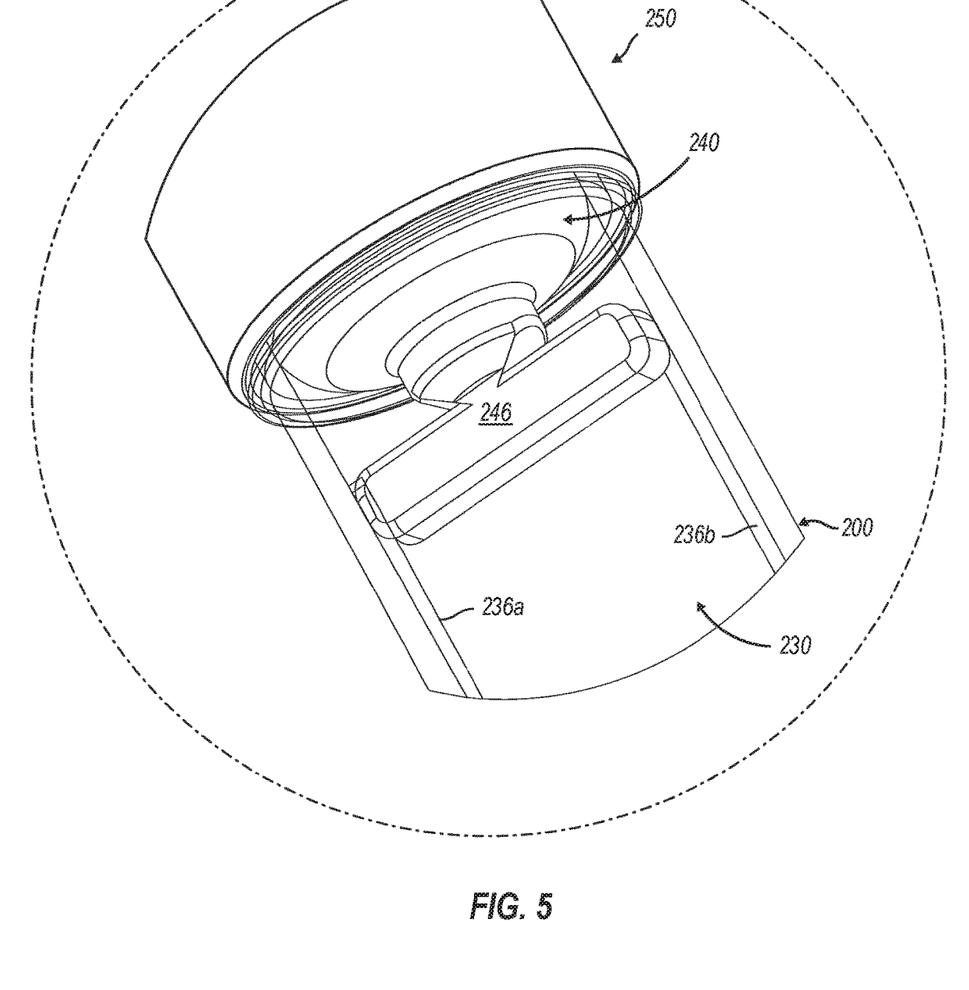
FIG. 5 illustrates a close-up view of an elongate or projecting member associating with two opposing elongate ridges within a sample collection chamber.

Instead of having a single elongate body associated with the breakable tip 146, FIG. 5 illustrates a breakable tip 246 that includes opposing elongate bodies that extend to interact with both ridges 236a, 236b of the sidewall. As solution cap 250 is rotated relative to collection vial 200, breakable tip 246 is restrained from rotation by first elongate ridge 236a and second elongate ridge 236b. As further rotation of solution cap 250 occurs (e.g., about 10 degrees of rotation), the breakable tip 146 is shorn away to reveal the spout 248 (as shown in FIG. 6).

It should be appreciated, however, that regardless of whether the breakable tip includes a single elongate body or a plurality of elongate bodies sized and shaped to interact with the elongate ridges of the sample collection chamber, the breakable tip is configured to engage and interlock with the elongate ridges or other functionally similar elements of the sample collection chamber. In some embodiments, therefore, this interaction is a preliminary step to causing the reagents to be released into the sample collection chamber. That is, in some embodiments, such as that shown in FIG. 6, the breakable tip 246 is broken off and is falling away from the solution cap 250. This allows preservation solution to flow from the reagent chamber 240 over the collected sample and preserve the probative component prior to the sample being tested.

Figure 6:
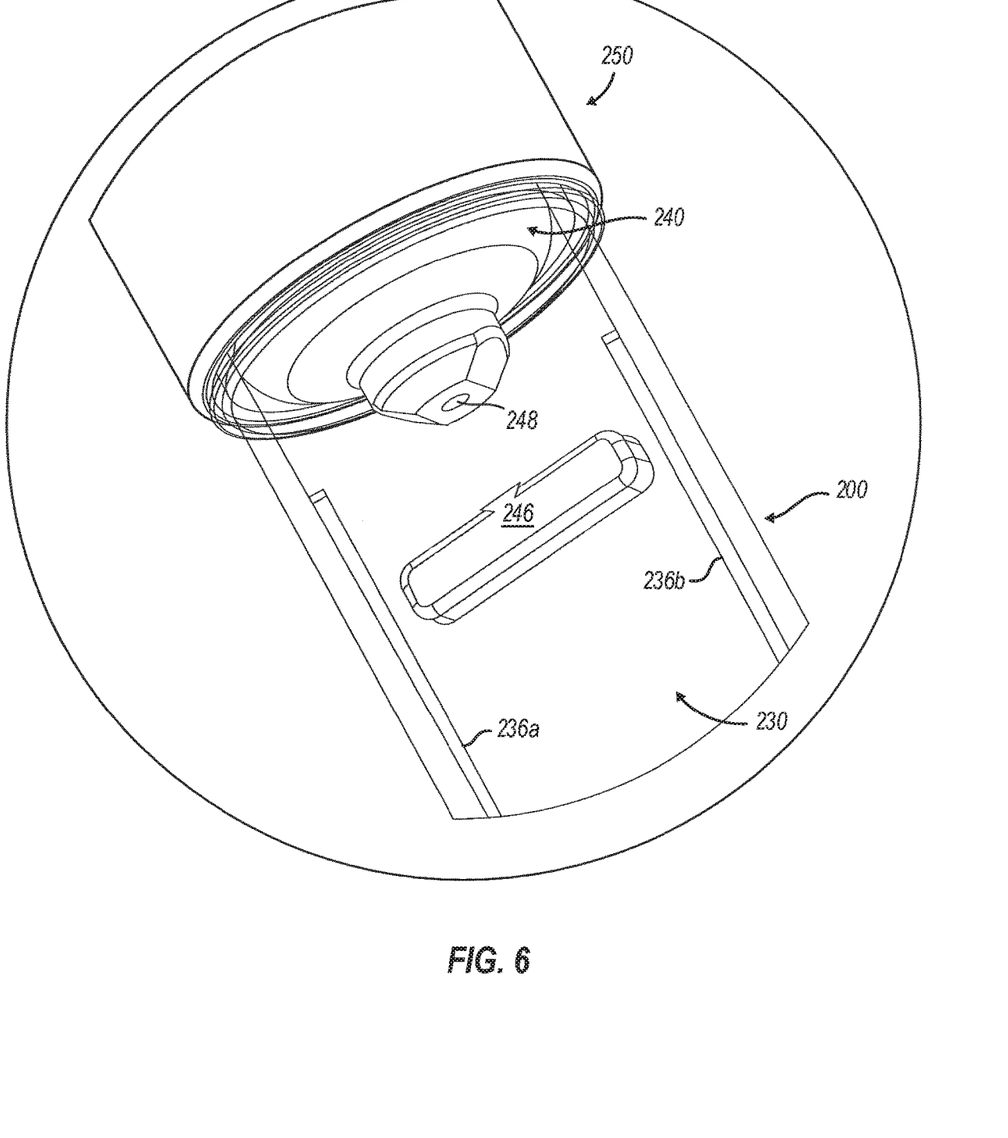
FIG. 6 illustrates the sample collection chamber of FIG. 5 with the elongate or projecting member detached from the fluid reservoir.

As shown in FIG. 6, the solution cap 250 secures to and seals the collection vial 200 by any means described herein or as known in the art. In this closed and sealed state, the collection vial 200 can be shaken to allow all or at least most of the preservation liquid to cover the collected sample. Additionally, the biological sample therewithin is protected from the outside atmosphere by being air- and water-tight. This reduces the chances of the sample contamination and helps maintain the integrity of the collected specimen during transportation to the laboratory.

Sample Collection Systems/Kits Having a Twist and Tear Mechanism

Figure 7:
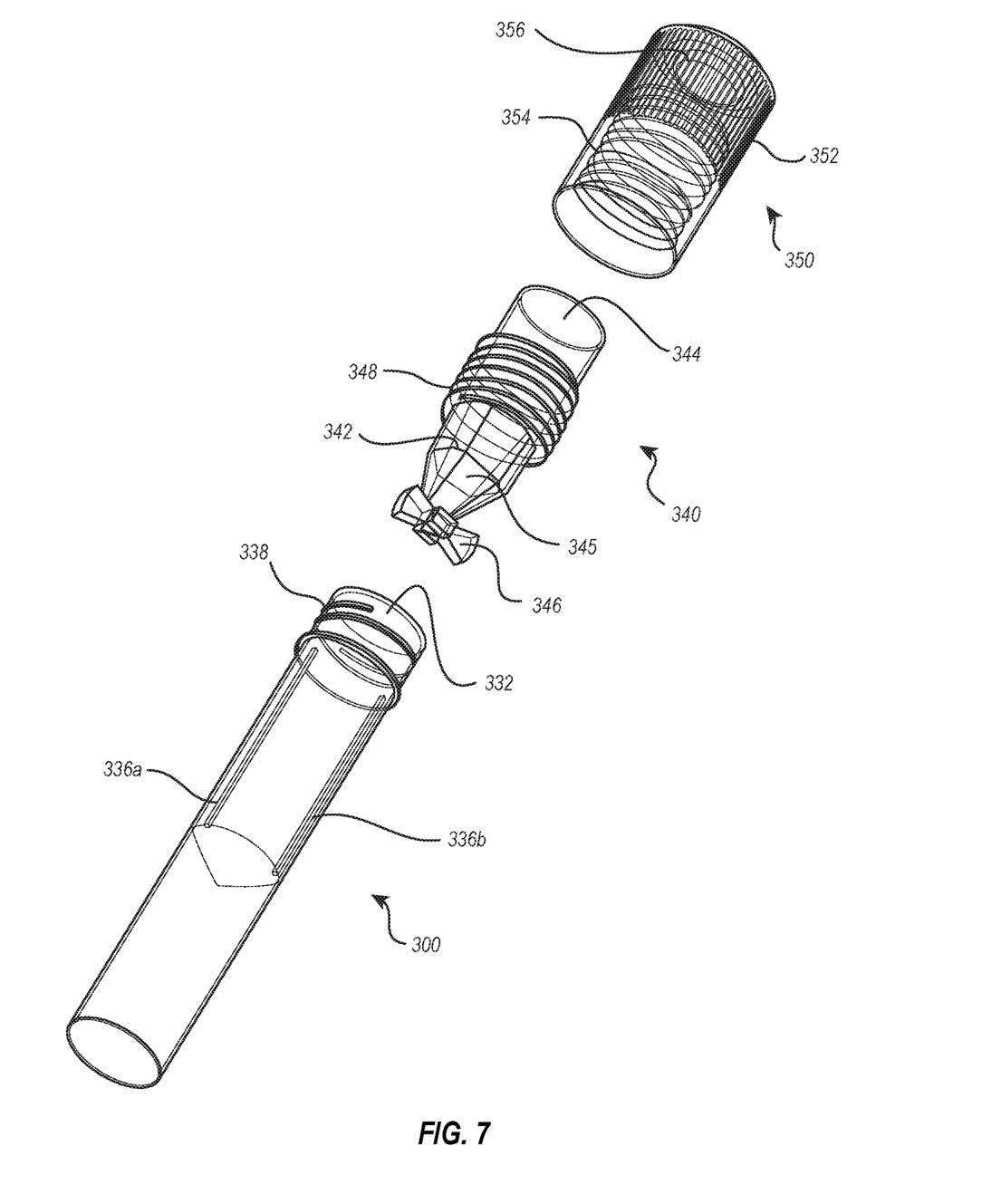
FIG. 7 illustrates an exploded perspective view of a sample collection system having a twist and tear mechanism.
Figure 8:
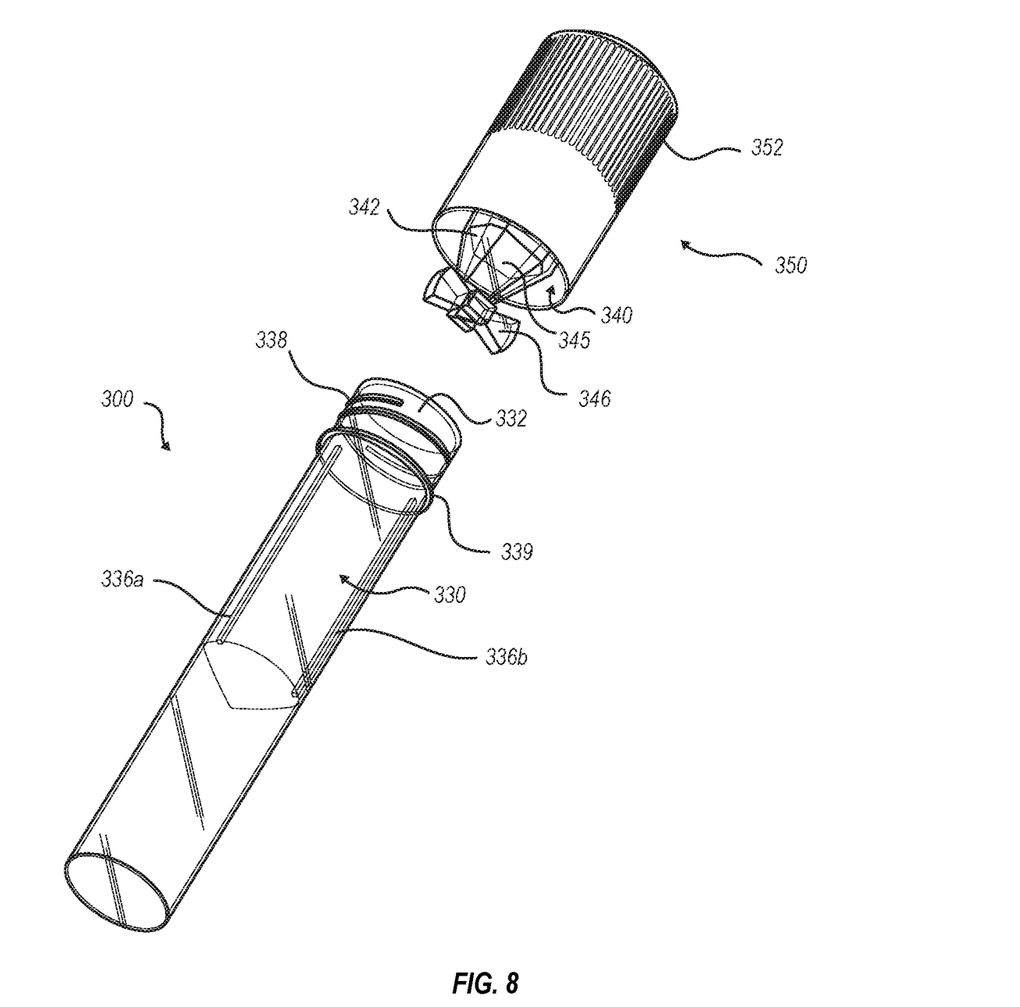
FIG. 8 illustrates a perspective view of the sample collection system of FIG. 7 in a partially assembled configuration.
Figure 9:
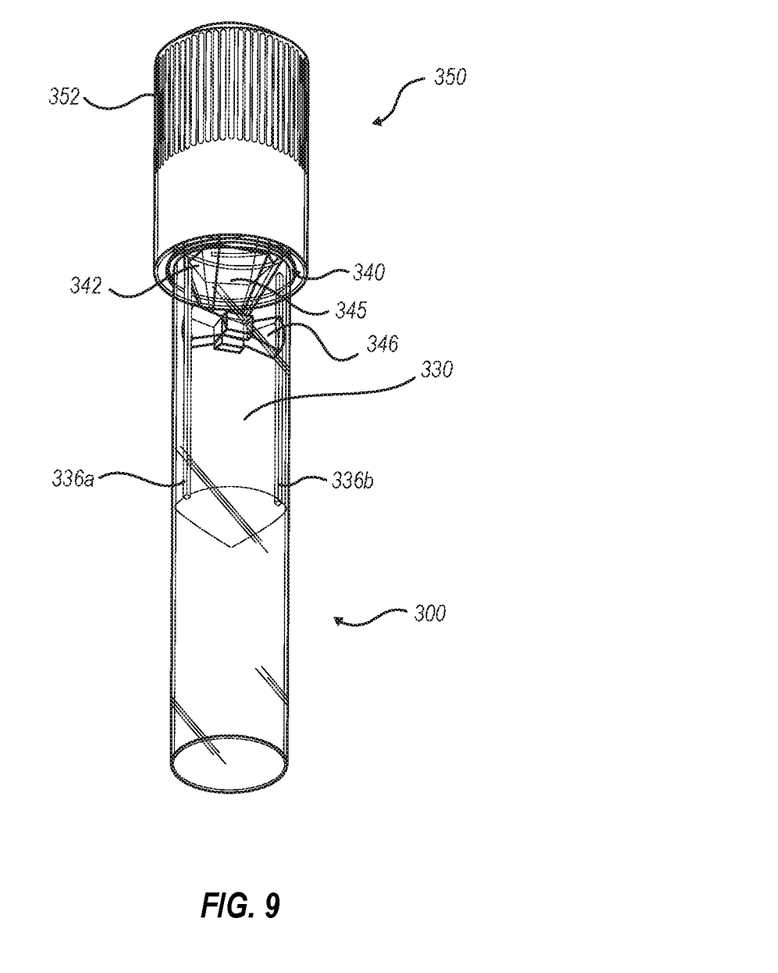
FIG. 9 illustrates a front elevation view of the sample collection system of FIGS. 7 and 8 in a further assembled configuration.

With reference to FIGS. 7-9, a sample collection kit can, in some embodiments, include a sample collection vial 300 and sealing cap 350 similar to that described above. However, instead of including a breakable tip, the sealing cap 350 can be associated with a fluid reservoir 340 having disposed at a closed end an elongate or projecting member 346 that engages ridges 336a, 336b on the interior sidewall of the sample collection chamber 330 as the sealing cap 350 is associated with the collection vial 300. As the sealing cap 350 is advanced in tighter association with the collection vial 300 by, for example, engaging interlocking threads (e.g., external threads 338 of the collection vial 300 and internal threads 354 of the solution cap 350), a sidewall of the fluid reservoir 340 becomes torn or ruptured in response to an angular stress resulting from the joinder of the solution cap 350 and the collection vial 300.

As more particularly illustrated in FIGS. 7-9, an exemplary sample collection kit similar to that previously described is provided in an exploded view (see FIG. 7), a partially assembled view (see FIG. 8), and a further assembled view (see FIG. 9). In general, the sample collection kit includes a sample collection vial 300, a fluid reservoir 340, and a sealing cap 350. The sample collection vial 300 includes a sample collection chamber 330, an opening 332 configured to receive a biological sample (e.g., with or without the assistance of a saliva funnel as discussed above), one or more elongate ridges 336a, 336b disposed along and projecting inwardly from an interior sidewall of the sample collection chamber, and a connection member 338 disposed on an exterior portion of the sample collection vessel. In some embodiments, the sample collection chamber 330 includes a conical base connected to a cylindrical body. It should be appreciated, however, that other geometries are considered within the scope of the invention. The sample collection chamber may include a polygonal geometry or an arcuate geometry or a combination thereof.

As illustrated in FIGS. 7-8, an exemplary sample collection kit can include a fluid reservoir 340 having a reagent chamber 342 that retains preserving or buffering reagents therein. The reagent(s) can be introduced through opening 344 and sealed therein by interengagement of the fluid reservoir 340 with the sealing cap 350. For example, as illustrated in FIGS. 7-8, the fluid reservoir 340 can be filled with an appropriate amount and type of reagent during manufacturing and/or assembly of the kits. The filled fluid reservoir 340 can then be associated with a sealing cap 350 to seal the reagents therein. As shown in FIGS. 7-8, the fluid reservoir can include threads 348 on an exterior surface and complementary threads 354 within sealing cap 350. The opening 344 of the fluid reservoir 340 can be advanced into the sealing cap 350 until the threads 348 and the complementary threads 354 engage at which point the fluid reservoir 340 is rotationally engaged with the sealing cap 350. The fluid reservoir can be advanced within the cap until an upper end thereof is tightly associated with a sealing mechanism located within the sealing cap 350.

As illustrated in FIGS. 7 and 8, the sealing mechanism can include an O-ring 356. Interaction between the opening 344 and the O-ring 356 creates a fluid tight seal, thereby retaining the reagents within the reagent chamber 342. In some embodiments, the fluid tight seal created between fluid reservoir 340 and the sealing cap 350 is additionally a gas tight seal, preventing dehydration or evaporation of reagents in the fluid reservoir 340 over time. Thus, once the fluid reservoir 340 is filled with the proper volume of reagent(s) at manufacturing/assembly of the sample collection kit, it can be advantageously stored with little to no loss of reagents from the fluid reservoir 340 (such as due to a loss resulting from spillage, dehydration, and/or evaporation). Additionally, or alternatively, the volume of space within the reagent chamber 342 can be pressurized when the opening 344 is sealed upon the sealing mechanism. Such pressure can beneficially act to expel preservation solution from the reagent chamber 342 when it is torn or ruptured.

The reagent compartment 342 is designed to be torn or ruptured during sealing of the collection vial 300 with the sealing cap 350. As shown in the figures, the fluid reservoir 340 includes an elongate member 346 disposed at a distal end thereof. Although the elongate member 346 is depicted in FIGS. 7-9 as two frustoconical prisms attached to a cuboid, it should be appreciated that the elongate member can take any of a variety of geometries and configurations. For example, the elongate member may have a single arm or a plurality of arms, with each arm being to each other arm in equidistant intervals or at irregular intervals. The elongate member may be V-shaped or resemble the spokes of a three-spoked wheel. Additionally, or alternatively, each arm of the elongate member can be a frustoconical prism, as illustrated in FIGS. 7-9, or it can be cuboid, cylindrical, or a truncated cylinder having a flat face that can associate with the elongate ridge(s).

Because the elongate member 346 is configured in size and shape to associate with and be interlocked by elongate ridges 336a, 336b of the sample collection chamber 330, it is in some ways similar to the breakable tip 146, 246 described above. However, as opposed to the breakable tip that is broken off to release reagents, the elongate member 346 is designed to retain association with the reagent chamber 342, even after the weakened, thinned, or frangible sidewall tears/ruptures. That is, in some embodiments, the elongate member 346 can remain associated with a portion of the sidewall at all times, whether the sidewall is intact or torn.

In some embodiments, the elongate ridges 336a, 336b disposed on an interior sidewall of the sample collection chamber 330 begin at or near the opening 332 and extend to the bottom of the sample collection chamber 330. In some embodiments, the elongate ridges span less than the entire length of the sidewall. For example, the elongate ridges may only be disposed along a brief portion of the sidewall at a position that allows engagement of an elongate member 346 (e.g., a laterally extending portion, such as one or more arms of an L- or T-shaped bar) when the sealing cap 350 is engaged with the sample collection vessel 300 and not before. In other words, in some embodiments, the sealing cap 350 may be loosely associated—though not threadedly engaged—with the sample collection vial 300, and the associated fluid reservoir 340 and elongate member 346 can spin freely within the sample collection chamber 330 without engaging the ridge(s) 336a, 336b (as shown, for example in FIG. 8). Yet, upon engagement of the sealing cap 350 with the connection member 338 of the sample collection vessel 300, the fluid reservoir 340 is drawn further within the sample collection chamber 330, and the elongate member 346 associated therewith is positioned to engage the ridges 336a, 336b on the interior sidewall of the sample collection chamber 330 (e.g., FIG. 9). It should be appreciated that in some embodiments, the elongate ridges 336a, 336b project into the sidewall of the sample collection chamber 330 such that the elongate member 346 is depressed within the ridge, becoming engaged therewith.

Additionally, or alternatively, the sidewall 345 can be torn from a point adjacent to or proximate the elongate member 346 and extending away from the elongate member 346. The weakened or thinned sidewall 345 can, in some embodiments, begin at or near the elongate member 346 and spiral directionally away from the elongate member 346. The weakened or thinned sidewall 345 can extend a partial or a full turn about the fluid reservoir 340 and can include a graded incline to any degree known in the art. Additionally, or alternatively, the weakened or thinned sidewall 345 can include a lower tensile strength than the elongate member 346 or other portions of the reagent chamber 342, causing it to mechanically fail (e.g., tear) before disfigurement of other elements or regions thereof.

The reagent(s) within the reagent chamber 342 (which can be the same or a different composition than the reagents 144 of FIGS. 1-6) can be introduced to a biological sample in the sample collection chamber 330 when the sidewall of the reagent chamber 342 is ruptured or torn during attachment of the sealing cap 350 to the sample collection vial 300. The sidewall of the reagent chamber 342 can include a weakened or thinned portion 345 along which the sidewall is torn.

For example, when the elongate member 346 interfaces and/or interlocks with elongate ridges 336a, 336b of the sample collection chamber 330 and the sealing cap 350 is further engaged with the sample collection vial 300, the rotational force is distributed through the elongate member 346 and to the weakened or thinned sidewall 345. The weakened or thinned sidewall 345, having a lower tensile strength than other portions of the reagent chamber 342, the elongate member 346, and/or the ridges 336a, 336b, will undergo a mechanical failure, causing the sidewall to tear and release the reagents within.

In some embodiments, the weakened or thinned portion of the sidewall 345 is duplicated on an opposing side thereof or a plurality of weakened or thinned sidewall portions are disposed about a bottom portion of the reagent chamber, adjacent to the elongate member 346. In the presence of one or more weakened or thinned sidewalls, the sidewalls may all tear or only a subset of the thinned or weakened sidewalls may tear. The thinned or weakened sidewalls may tear concurrently or sequentially. In some embodiments, the elongate member 346 remains attached to at least a portion of the reagent chamber 342 such that the elongate member does not fall into the sample collection chamber 330 when the sidewall 345 is torn.

After the sidewall has been torn, the reagents are at least mostly deposited into the sample collection chamber 340 where they can mix with a biological sample contained therein, preserving the probative component for later processing. The sealing cap 350 can be further associated with the collection vial 300 to form a liquid tight seal. In some embodiments, the sealing cap 350 can make a gas tight seal when associated with the collection vial such that the intermixed biological sample and reagents do not dehydrate and/or evaporate. This can advantageously allow the sealed biological sample to be preserved for later processing for a longer period of time (e.g., weeks or months).

In some embodiments, the solution cap 350 and the collection vial 300 are connected via connection members other than complementary threads. For example, the solution cap 350 may include a wedge (circumferential or two or more opposing wedges) disposed on an interior sidewall of the solution cap that when pressed over the collection vial 300 secures around a lip 339 on the collection vial 300, sealing the sample collection chamber 330. The solution cap can then be spun/rotated so that an associated elongate member 346 engages one or more ridges 336a, 336b protruding inwardly from an interior sidewall of the collection vial 300. Continued rotation of the solution cap 350 causes a thinned, weakened, or frangible sidewall 345 to fracture, releasing the reagents held therein.

As shown in FIGS. 7-9, the solution cap 350 may additionally include a plurality of external ridges 352. The external ridges 352 can allow a user to better grip the solution cap 350 while positioning the cap 350 on top of collection vial 300. Additionally, or alternatively, the external ridges 352 can be used to rotate and/or close the solution cap 350 onto collection vial 300. In some embodiments, it may be beneficial to enable the user to more forcefully torque the solution cap 350, and the external ridges 352 can provide the user with a better grip, enabling them to do so.

Unless defined otherwise, all technical and scientific terms used herein have the same meaning as commonly understood by one of ordinary skill in the art to which the present disclosure pertains.

It will also be appreciated that systems, devices, products, kits, methods, and/or processes, according to certain embodiments of the present disclosure may include, incorporate, or otherwise comprise properties, features (e.g., components, members, elements, parts, and/or portions) described in other embodiments disclosed and/or described herein. Accordingly, the various features of certain embodiments can be compatible with, combined with, included in, and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include said features, members, elements, parts, and/or portions without necessarily departing from the scope of the present disclosure.

Moreover, unless a feature is described as requiring another feature in combination therewith, any feature herein may be combined with any other feature of a same or different embodiment disclosed herein. Furthermore, various well-known aspects of illustrative systems, methods, apparatus, and the like are not described herein in particular detail in order to avoid obscuring aspects of the example embodiments. Such aspects are, however, also contemplated herein.

The present disclosure may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached disclosure for purposes of illustrating embodiments of the present disclosure, it will be apparent to those skilled in the art that various changes in the methods, products, devices, and apparatus disclosed herein may be made without departing from the scope of the disclosure or of the invention, which is defined in the appended claims. All changes which come within the meaning and range of equivalency of the claims are to be embraced within their scope.

What is claimed is:

1. A biological sample collection system, comprising:
   a sample collection vessel, the sample collection vessel comprising:
     a sample collection chamber, the sample collection chamber having an opening that is configured to receive the biological sample into the sample collection chamber;
     one or more ridges disposed along and projecting inwardly from an interior portion of the sample collection chamber; and
     a connection member disposed on an exterior portion of the sample collection vessel;
   a fluid reservoir, the fluid reservoir comprising:
     a reagent chamber, the reagent chamber having an open end and a closed end;
     an elongate member disposed at the closed end of the reagent chamber, the elongate member sized and shaped to engage at least one of the one or more ridges of the sample collection vessel when positioned within the sample collection chamber; and
     external threads disposed on an exterior portion of the fluid reservoir; and a sealing cap, the sealing cap comprising:
     internal threads configured to engage the external threads of the fluid reservoir; and
     a complementary connection member configured to associate with the connection member of the sample collection vessel to couple the sample collection vessel and the sealing cap.

2. The biological sample collection system as in claim 1, further comprising a sealing member disposed within the sealing cap, the sealing member configured to engage the fluid reservoir to seal the open end of the reagent chamber within the sealing cap.

3. The biological sample collection system as in claim 2, wherein the sealing member comprises an O-ring.

4. The biological sample collection system as in claim 1, wherein the reagent chamber comprises a weakened or thinned sidewall.

5. The biological sample collection system as in claim 4, wherein at least a portion of the weakened or thinned sidewall is positioned adjacent to the elongate member.

6. The biological sample collection system as in claim 1, wherein the connection member comprises a ridge projecting away from the sample collection vessel or a depression within the sample collection vessel and the complementary connection member comprises a hook or ridge sized and shaped to engage the connection member.

7. The biological sample collection system as in claim 1, wherein the connection member and the complementary connection member comprise threads.

8. The biological sample collection system as in claim 7, wherein the threads of the complementary connection member comprise the internal threads of the sealing cap.

9. The biological sample collection system as in claim 1, wherein the one or more elongate ridges comprise two elongate ridges disposed opposite each other on the interior portion of the sample collection chamber, and wherein opposite faces of the elongate member are configured to engage the two elongate ridges.

10. The biological sample collection system as in claim 1, wherein the sample collection system comprises a separable two-piece sample collection system, the sample collection vessel comprising a first piece of the separable two-piece sample collection system, and the fluid reservoir and the sealing cap—together—comprising a second piece of the separable two-piece sample collection system.

11. A method for collecting and preserving a biological sample, comprising:
    providing or obtaining the biological sample collection system of claim 1;
    receiving a biological sample through the opening of the sample collection chamber;
    placing the fluid reservoir into the opening of the sample collection chamber;
    engaging the elongate member of the fluid reservoir with the one or more ridges disposed along and projecting inwardly from the interior portion of the sample collection chamber; and
    rotating the fluid reservoir to disestablish a sidewall of the fluid reservoir, thereby releasing reagents held within the fluid reservoir into the sample collection chamber.

12. The method as in claim 11, wherein rotating the fluid reservoir causes the elongate member to become detached from the fluid reservoir, the reagents being released through an aperture created by detachment of the elongate member.

13. The method as in claim 11, wherein the elongate member is engaged with the one or more elongate ridges such that the fluid reservoir is rotationally locked in a first direction and the rotating step is performed in the first direction.

14. The method as in claim 11, wherein disestablishing the sidewall of the fluid reservoir comprises rotating the fluid reservoir causes a causing the sidewall of the fluid reservoir to tear.

15. The method as in claim 14, wherein the tearing of the sidewall occurs along a weakened or thinner portion of the fluid reservoir.

16. The method as in claim 15, wherein the fluid reservoir is associated with the sealing cap, and wherein rotating the fluid reservoir seals the sample collection chamber.

17. A kit for collecting and preserving a biological sample, comprising:
- a sample collection vessel, the sample collection vessel comprising:
  - a sample collection chamber having an opening configured to receive the biological sample from a user into the sample collection chamber;
  - a first elongate ridge and a second elongate ridge disposed longitudinally and projecting inwardly from an interior portion of the sample collection chamber, the first elongate ridge being disposed opposite the second elongate ridge; and
  - a threaded connection member disposed on an exterior portion of the sample collection vessel and adjacent to the opening; and
- a sealing cap, the sealing cap comprising:
  - a sealing member;
  - a reagent chamber comprising:
    - a proximal end associated with the sealing member;
    - a distal end having an elongate member, wherein the elongate member has one or more laterally extending portions; and
    - an interior region comprising a measure of reagents; and
    - internal threads configured to engage the threaded connection member of the sample collection vessel;
    - wherein the one or more laterally extending portions of the elongate member is sized and shaped to engage at least one of the first or second elongate ridges when arranged within the sample collection chamber.

18. The kit as in claim 17, wherein a portion of the reagent chamber comprises a weakened or thinned sidewall.

19. A biological sample collection system, comprising:
- a sample collection chamber comprising an opening disposed at a top portion of the sample collection chamber and an elongate ridge disposed along and projecting inwardly from an interior sidewall of the sample collection chamber;
- a reagent chamber having a frangible sidewall selectively connected to the sample collection chamber, the reagent chamber comprising an elongate member extending laterally and disposed at a closed end of the reagent chamber, the elongate member sized and shaped to engage the elongate ridge of the sample collection chamber and tear the frangible sidewall when arranged within the sample collection chamber; and
- a sealing cap comprising a connection mechanism configured to associate with and seal one or more of the sample collection chamber and the reagent chamber.

* * * * *

UNITED STATES PATENT AND TRADEMARK OFFICE
CERTIFICATE OF CORRECTION

Page 1 of 1

PATENT NO. : 10,525,473 B2
APPLICATION NO. : 15/667228
DATED : January 7, 2020
INVENTOR(S) : Kevin Gregg Williams It is certified that error appears in the above-identified patent and that said Letters Patent is hereby corrected as shown below:

In the Specification

<u>Column 6</u>
Line 26, change "The" to –the–
Line 33, change "protect" to –protects–

In the Claims

<u>Column 15</u>
Line 3, removes [causes a]

Signed and Sealed this
Second Day of June, 2020

Andrei Iancu
*Director of the United States Patent and Trademark Office*